United States Patent
Frederico et al.

(10) Patent No.: US 7,825,159 B2
(45) Date of Patent: Nov. 2, 2010

(54) MIXTURES OF AROMATIC ESTERS FOR MARKING OR TAGGING ORGANIC PRODUCTS, MARKER COMPOSITIONS COMPRISING THE SAME AND MANUFACTURING METHODS THEREOF

(75) Inventors: Justin J. Frederico, Yardley, PA (US); Bharat Desai, Ringwood, NJ (US); Michael J. Smith, Newtown, PA (US); Michael P. Hinton, Richboro, PA (US)

(73) Assignee: United Color Manufacturing, Inc., Newtown, PA (US)

( * ) Notice: Subject to any disclaimer, the term of this patent is extended or adjusted under 35 U.S.C. 154(b) by 1 day.

(21) Appl. No.: 12/000,072

(22) Filed: Dec. 7, 2007

(65) Prior Publication Data

US 2008/0139646 A1  Jun. 12, 2008

(30) Foreign Application Priority Data

Dec. 7, 2006 (KR) .................... 10-2006-0123813

(51) Int. Cl.
*A01N 43/08* (2006.01)

(52) U.S. Cl. ..................................... 514/470
(58) Field of Classification Search .................. 514/470
See application file for complete search history.

(56) References Cited

U.S. PATENT DOCUMENTS

| | | | | |
|---|---|---|---|---|
| 4,163,762 A | * | 8/1979 | Rudd | 525/67 |
| 5,672,182 A | * | 9/1997 | Smith | 44/349 |
| 2003/0129758 A1 | * | 7/2003 | Smith et al. | 436/56 |

* cited by examiner

*Primary Examiner*—D. Margaret Seaman
*Assistant Examiner*—Nizal S Chandrakumar
(74) *Attorney, Agent, or Firm*—Kelley Drye & Warren, LLP

(57) ABSTRACT

The present invention is directed to a mixture of at least two different alkylated phenolphthalein ester compounds. Specifically, the present invention is directed to a mixture of at least two different compounds of formula I:

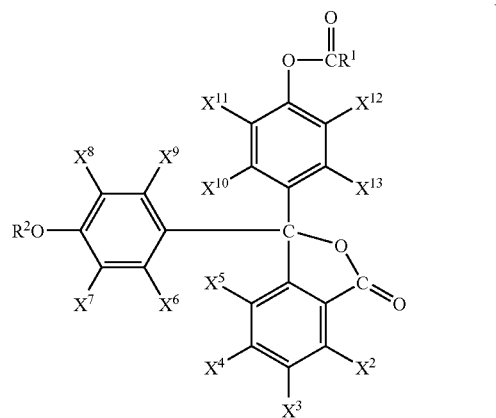

wherein $R^1$ represents a straight chain alkyl group having 1 to 11 carbon atoms; $R^2$ represents a hydrogen atom or a group of the formula $C(O)R^4$ where $R^4$ is a hydrogen atom or a straight chain alkyl group having 1 to 11 carbon atoms; $X2$-$X5$ independently represent hydrogen; $X6$-$X13$ is same or different, and represents hydrogen or a straight or branched chain alkyl group having 1 to 12 carbon atoms. It further relates to a marker composition containing said mixtures dissolved in a solvent.

12 Claims, No Drawings

MIXTURES OF AROMATIC ESTERS FOR MARKING OR TAGGING ORGANIC PRODUCTS, MARKER COMPOSITIONS COMPRISING THE SAME AND MANUFACTURING METHODS THEREOF

CROSS REFERENCE TO RELATED PATENT APPLICATIONS

This application claims priority on Korean Patent Application No. 10-2006-0123813, entitled "Mixtures of Aromatic Esters for Marking or Tagging Organic Products, Marker Compositions Comprising the Same and Manufacturing Method Thereof," filed in the Korean Intellectual Property Office on Dec. 7, 2006, which is hereby incorporated by reference in its entirety.

TECHNICAL FIELD

The present disclosure relates to mixtures of compounds useful for marking or tagging various products such as petroleum fuels or solvents and to compositions and methods associated therewith.

BACKGROUND

Markers are substances which are used to tag products, typically petroleum products, for subsequent detection. The markers are normally dissolved in liquids to be identified, then subsequently detected by performing a simple physical or chemical test on the tagged liquids. Applications of markers include use by the government to ensure that the appropriate tax has been paid on particular fuels. Oil companies also mark their products to help identify those who have altered their products.

Markers have been used in petroleum products for many years. Many have proven extremely useful in providing definite means of identifying particular fuels for the purpose of criminal activity and theft. For example, U.S. Pat. No. 6,482,651 discloses a class of alkylated phenolphthalein esters that are particularly useful in this manner due to their ease of use and ease of testing. However, such marker compounds suffer a disadvantage in that they must be formulated with large amounts of co-solvents in order to, first, stabilize the concentrated solutions that are most desirable for markers of this type; and, second, to aid in the dispersion of the marker into the petroleum fluid to achieve the low dosage rate (<20 ppm) usually employed with fuel markers.

The co-solvents most often used are polar aprotic solvents. N-octylpyrolidinone, N-methylpyrolidinone, dimethylsulfoxide, dimethylformamide have proven especially well suited. The problem is one of cost. That is, these aprotic solvents are much more expensive than petroleum based hydrocarbon solvents. The aprotic solvent may be used at anywhere from 25 to 35 wt. % of the marker composition. Cresolphthalein dibutyrate, as taught in U.S. Pat. No. 6,482,651, requires at least 28 wt. % n-octylpyrolidinone. Otherwise, the phthalein precipitates on standing overnight in the freezer and will not disperse into diesel fuel even with vigorous stirring. One good test for solubility is to combine 10% by weight phthalein into kerosene. Kerosene is a very difficult solvent to work with. It has very non-polar characteristics and most dyes and markers have very poor solubility in pure kerosene.

In view of the above, it would be desirable to provide marker compounds which require less or zero co-solvents to achieve the desired stability and dispersion characteristics.

SUMMARY

An embodiment of the present invention is directed to a mixture of at least two different alkylated phenolphthalein ester compounds. Specifically, the present disclosure is directed to a mixture of at least two different compounds of formula I:

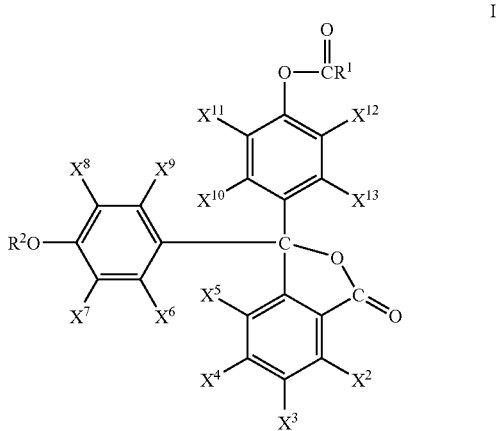

wherein $R^1$ represents a straight chain alkyl group having 1 to 11 carbon atoms; $R^2$ represents a hydrogen atom or a group of the formula $C(O)R^4$ where $R^4$ is a hydrogen atom or a straight chain alkyl group having 1 to 11 carbon atoms; X2-X5 independently represent hydrogen; X6-X13 is same or different, and represents hydrogen or a straight or branched chain alkyl group having 1 to 12 carbon atoms. It further relates to a marker composition containing said mixtures dissolved in a solvent.

An embodiment of the present invention relates to the use of the markers comprising a mixture of at least two compounds of formula I in forming marked compositions. The marked compositions comprise an organic product such as a petroleum product or an organic solvent and a detectable amount of a marker comprised of the above. These marked compositions can be identified by adding a developing reagent to a sample thereof which forms color in or changes the color of the sample. In one embodiment, a petroleum product can be identified by adding a developing agent and subsequently extracting the developed marker in an extraction medium.

The present disclosure is based on the discovery that the mixtures of at least two compounds of formula I provide a remarkable improvement over previously disclosed marker compounds in that they may be manufactured and formulated without the use of any co-solvent. Further, they may be formulated at higher concentrations than is the case with prior art chemicals because of this improved solubility.

DETAILED DESCRIPTION

In the following description, numerous specific details are set forth. It will be apparent, however, that these embodiments may be practiced without some or all of these specific details. In other instances, well known process steps or elements have not been described in detail in order not to unnecessarily obscure the disclosure.

An embodiment of the present invention is a mixture of at least two different alkylated phenolphthalein ester compounds. Specifically, the present disclosure is directed to a mixture comprising at least two different compounds of formula I:

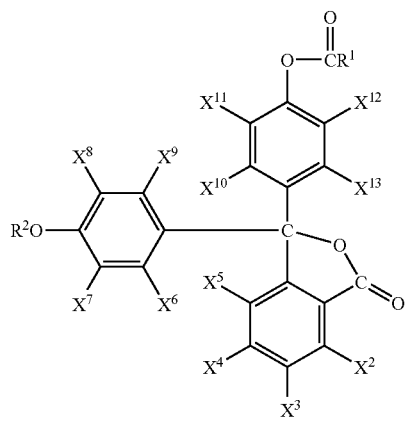

I wherein $R^1$ represents a straight chain alkyl group, containing 1 to 11 carbon atoms, preferably, 3 to 7 carbon atoms, more preferably, 3 to 6 carbon atoms, and most preferably 6 carbon atoms. Examples of alkyl groups include propyl, butyl, pentyl, hexyl, heptyl and isomers thereof, but it is not limited thereto.

The $OR^2$ moiety is preferably in the 4-position or 2-position, and more preferably in the 4-position. $R^2$ represents a hydrogen atom or a group of the formula $C(O)R^4$ where $R^4$ is a hydrogen atom or a straight chain alkyl group, containing 1 to 11 carbon atoms, preferably, 3 to 7 carbon atoms, more preferably, 3 to 6 carbon atoms, and most preferably 6 carbon atoms. The alkyl groups $R^1$ and $R^4$ may be the same or different. The esters are also much more resistant to inadvertent removal from the petroleum product than their unesterified counterparts.

$X^2$—$X^5$ represents hydrogen, and $X^6$—$X^{13}$ is same or different, and represents hydrogen or a straight or branched chain alkyl group, containing 1 to 12 carbon atoms, preferably 1 to 5 carbon atoms. Preferably, one or two of $X^6$ to $X^9$ are alkyl and the others are hydrogen, while one or two of $X^{10}$ though $X^{13}$ are alkyl and the others are hydrogen. More preferably, one of $X^7$ and $X^8$ is methyl, propyl or butyl, one of $X^{11}$ and $X^{12}$ is methyl, propyl or butyl, and other X groups are hydrogen.

The lactone ring of the compounds of formula I may be readily or instantaneously opened under some conditions and form a carboxylic acid group. Therefore, it should be understood that the compounds of formula I are in equilibrium with those of formula II shown below:

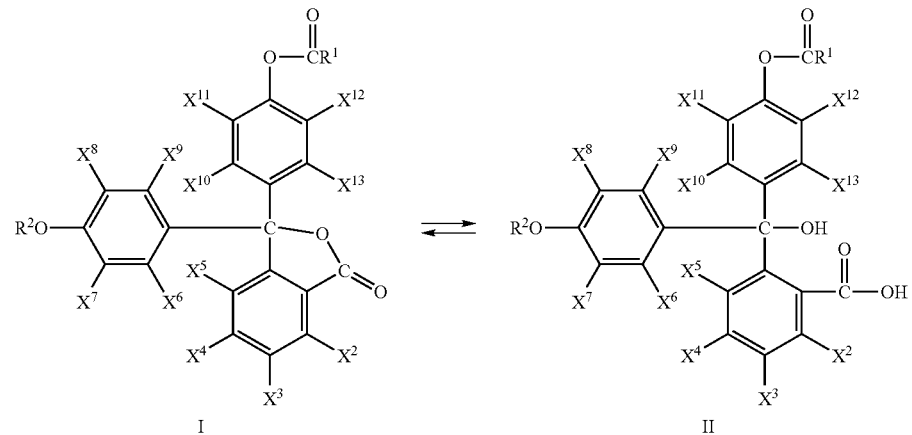

I II

Under most circumstances, the formation of the lactone forms (I) are greatly preferred. The lactones are advantageous in that they increase resistance to inadvertent removal of the markers and minimize the overall color of the undeveloped substances.

The mixtures of two or more compounds of formula I can be prepared from the reaction of two or more phenols with phthalic anhydride, and subsequently esterifying with anhydrides or by reaction generally known within the art starting from known or commercially available starting materials. Preferably, a mixture of methylphenol, propylphenol and butylphenol may be used with a single anhydride, followed by subsequent esterification with butyric anhydride, to also yield a composition that requires zero co-solvent. Mixtures of anhydrides are also useful in that they allow more concentrated solutions to be prepares. The formation of the compounds of formula I is not limited thereto and other ways for forming the same will be readily apparent to the worker of ordinary skill in the art.

In one embodiment, in the mixture of two or more different alkylated phenolphthalein ester compounds, one of alkylated phenolphthalein ester compounds comprises at least about 10% by weight based on the total weight of the mixture, and another ester compound in the mixture also comprises at least about 10% by weight based on the total weight of the mixture. Preferably, one of the alkylated phenolphthalein ester compounds in the mixture comprises at least about 25% by weight based on the total weight of the mixture, and another ester compound in the mixture comprises at least about 25% by weight based on the total weight of the mixture. More preferably, minimum amount of each alkylated phenolphthalein ester compounds in the mixture is not less than about 25% by weight.

Further, the mixture of three or more different alkylated phenolphthalein ester compounds is preferable. Furthermore, lower molecular weight also improves the sensitivity by providing higher strengths per given weight of marker.

The mixture according to an embodiment of the present invention can be used as markers in organic products, typically petroleum products and other organic solvents as a means to identify the petroleum product or solvent by color development. The petroleum products include fuels, lube oils and greases. The marker mixture may be added to the petroleum product in dry form as a powder or crystals or as a liquid solution concentrate. Liquid forms, such as concentrate solution, are usually preferred. The availability of marker compounds to be stable, free-flowing liquids makes them much more attractive to the petroleum industry than dry or solid products primarily because liquids are easier to handle. Dry or solid forms of markers can, however, be used directly. Examples of liquid petroleum products that can be marked by the mixtures of the present disclosure are gasoline, diesel fuel, fuel oil, kerosene and lamp oil. A preferred petroleum product is diesel fuel, which is composed principally of linear, branched or cyclic alkanes. Suitable solvents for use with liquid petroleum products include aromatics solvents, for instance, aromatic hydrocarbons, including alkyl benzenes such as xylene, and naphthalenes as well as aromatic alcohols.

The marker mixtures of an embodiment of the present invention provide a marked improvement over previously disclosed marker compounds (which must be dissolved or diluted into at least an equal weight of a co-solvent, to create a non-aqueous solution that has a high solubility in petroleum products) in that they may be manufactured and formulated without the use of any or less amount of co-solvent than required for the previously disclosed marker compounds. They may also be formulated at higher concentrations than is the case with prior art chemicals because of this improved solubility. The markers comprising a mixture of at least two compounds of formula I, quite surprisingly, serve to stabilize the marker composition (concentrate solution) and disperses into the petroleum product even without any co-solvent or with less than the usual amount of about 28% minimum of co-solvent.

In one embodiment, a 10% to 75% of active mixture according to the present invention may need no co-solvent, such as pyrolidinone, to form a completely stable solution even under prolonged storage conditions at −25 C. This marker composition may be added directly to kerosene of diesel fuel to achieve the required dosage rate. 10% solutions in kerosene can be readily made.

In another embodiment, a marker composition (liquid concentrate solution) may generally comprise about 1-30% by weight of the mixture according to the present invention in an aromatic solvent, based on the total weight of marker composition. Preferable ranges for the composition are about 15-25%, and usually from about 20-25% of the mixture according to an embodiment of the present invention, based on the total weight of marker composition. The aromatic solvent used in a particular marker composition will be selected based upon the type of petroleum product that is to be marked. For instance, a more volatile solvent will be chosen to mark gasoline products and a less volatile solvent will be used in marker compositions used to mark and identify diesel or home heating oil products.

In other embodiment, the marker composition comprises about 42-99% by weight of an aromatic solvent; about 1-30% by weight of a mixture comprising at least two different alkylated phenolphthalein ester compounds; and about 0-27% by weight of co-solvent, wherein the alkylated phenolphthalein ester compound is selected from the group of compounds represented by formula I.

The marker is added to an organic product to be marked or tagged in a detectable amount. A "detectable amount" of the marker is an amount that allows for detection of the developed marker by visual observation, spectroscopic instrumentation, or liquid chromatography either in the marked organic product or in an aqueous extraction medium. Spectrophotometer scans, generally in the visible range, may be interpreted in the regular absorbance/transmittance modes. But, where there is significant solvent background color, the results are preferably interpreted by the second derivative mode or method. Typically, the amount of marker present in an organic product ranges from at least about 0.05 ppm to 50 ppm, more commonly from about 0.1 ppm to 10 ppm and most preferably at a level of about 0.5 ppm to about 5 ppm.

Because the markers of the present invention are colorless or essentially colorless and soluble in organic products, their presence is detected by reacting them with a developer or developing reagent. For use in an embodiment of the present invention, the developing reagent may be, but is not limited to, an electron donating compound such as a base, preferably a strong base such as an alkali metal hydroxide, or most preferably a quaternary alkyl ammonium hydroxide. The developing reagent is generally added to a sample of the marked product so as to form a concentration of at least about 100 ppm, more typically about 500-10000 ppm, and more typically about 1000 to about 5000 ppm. The presence of base reactable substances such as acids in the marked product can compete for the developer reagent and thereby require more developer reagent to be added.

The developer reagent is preferably dissolved in a solvent that is miscible with the marked sample to form a developer composition. Typically, the developer comprises about 1%-10%, more preferably about 2%-5%, by weight, of the developing reagent. The volume ratio of developer added to a sample is preferably between about 1/100 and 1/2, and more preferably is between about 1/20 and 1/5. The developer composition may further comprise a buffering agent in order to assist in controlling the development conditions and specifically to suppress over-development.

After addition of the developer reagent, the sample is inspected to determine whether the developed marker is present therein. This inspection may be visually carried out with the unaided eye or with appropriate instrumentation such as ultraviolet, visible or infrared absorption spectrophotometers or liquid chromatography. The determination may be qualitative or quantitative, the latter allowing for the detection of dilution of the marked product. Furthermore, because the markers of the present invention form water soluble anions upon reaction with the developing reagent, the markers can be concentrated into an aqueous extraction medium.

Provided that only a qualitative indication of the presence of the marker is required, the now colored, "developed," fuel sample may be returned to its source. In this way, the developing reagent and marker are burned or used up with the product so that no potentially hazardous waste from, say, a roadside test, accumulates for disposal. Prior to returning the marker-developed fuel sample to its original source, the marker may be rendered colorless once again by the addition of a fuel miscible acid, preferably an organic carboxylic acid such as oleic or iso stearic acid. In this way fuel at the original source will not be color contaminated by the addition of "developed" fuel which may contain active, unreacted developer.

Alternatively, the colored marker may be rendered more visible by extraction from the developed fuel sample into an extraction medium. This may be accomplished by addition of water alone as an extraction medium to the sample, but the use of mixtures of water and a phase separation enhancer such as aliphatic alcohols, glycols, or glycol ethers are preferred. Use of a phase separation enhancer promotes an easier separation of the aqueous and organic phases. Typically the extraction medium is added to the petroleum sample in a ratio of about 1% to about 20% by volume. Additionally, other substances, for example pH buffer salts, may be present in the extractant phase to stabilize the colored anion or marker. For example, the extraction medium further comprises a developing reagent such as quaternary alkyl ammonium hydroxide compounds to provide a one step method for developing and extracting the marker. Other strong bases, of course, may be used, particularly alkali metal hydroxides. The use of extraction is preferred when the color of the developed marker is obscured by other coloring agents in the petroleum product or when the concentration is low.

The following examples are presented to provide a more detailed understanding of the invention. The examples are representative, and are not intended to limit the scope of the invention. Unless indicated otherwise, percent (%) is based on weight.

EXAMPLES

TABLE 1

Phenols and Anhydrides Used

| Mixture Number (Example Number) | Phenols Used | Anhydrides Used |
|---|---|---|
| 1 | 0-Cresol and o-sec-butyl Phenol | Heptanoic Anhydride |
| 2 | 0-Cresol and o-sec-butyl Phenol | Heptanoic Anhydride |
| 3 | 0-Cresol and o-sec-butyl Phenol | Heptanoic Anhydride |
| 4 | 0-Cresol and o-sec-butyl Phenol | Hexanoic Anhydride |
| 5 | 0-Cresol and o-sec-butyl Phenol | Heptanoic and Hexanoic Anhydrides |
| 6 | o-Cresol and o-isopropyl phenol | Heptanoic Anhydride |
| 7 | o-Cresol and o-isopropyl phenol | Butyric and hexanoic anhydrides |
| 8 | o-Cresol, o-sec butyl, and o-isopropyl phenol | Butyric Anhydride |
| 9 | o-Cresol, o-sec butyl, and o-isopropyl phenol | Heptanoic Anhydride |
| 10 | o-Cresol, o-sec butyl, and o-isopropyl phenol | Butyric, hexanoic and heptanoic anhydrides |

Example 1

Preparation of Mixture of o-Cresolphthalein diheptanoate and o-Butylphthalein diheptanoate A 2 liter flask fitted with stirrer, thermometer and heating mantel is charged with 100 grams of phthalic anhydride, 110 grams of methanesulfonic acid, and 98.8 grams of o-cresol and 45.8 grams of o-sec-butylphenol. The mixture is stirred and heated to 100-105° C. for 20 hours. The reaction mixture is then drowned into 800 grams of ice and water mixture. The pH of the reaction mixture is then adjusted to 9-10 by addition of 25% sodium hydroxide while maintaining a temperature below 60° C. Aromatic® 200, 300 grams, is now added to the aqueous suspension of the mixture of phthaleins. The reaction mixture is made highly alkaline by addition of 225 grams of 25% sodium hydroxide and then esterified by slow addition of 342 grams n-heptanoic anhydride maintaining a temperature below 50° C. and a pH of 10 or higher. The reaction mixture is then stirred till esterification is complete, as determined by thin layer chromatography. The reaction mixture is then heated to 90° C. and transferred to a separatory funnel where the layers are allowed to separate. The lower aqueous phase is removed and discarded while the upper organic phase containing the mixture of esterified phthaleins is dried free of water by heating it under vacuum to a temperature of 120° C. The dried product is further diluted with Aromatic® 200 to a weight of 1000 grams. The product is then filtered to remove any suspended insoluble material.

Example 2

Preparation of Mixture of o-Cresolphthalein diheptanoate and o-Butylphthalein diheptanoate The same procedure was followed as in Example 1 except 87.0 g of o-cresol and 62.2 g of o-sec-butylphenol were used, thus reducing the molar ratio of cresol to butylphenol from 3:1 to 2:1.

Example 3

Preparation of Mixture of o-Cresolphthalein diheptanoate and o-Butylphthalein diheptanoate The same procedure was followed as in Example 1 except 65.9 g of o-cresol and 91.5 g of o-sec-butylphenol were used, thus reducing the molar ratio of cresol to butylphenol from 3:1 to 1:1.

Example 4

Preparation of Mixture of o-Cresolphthalein dihexanoate and o-Butylphthalein dihexanoate A 2 liter flask fitted with stirrer, thermometer and heating mantel is charged with 100 grams of Phthalic anhydride, 110 grams of methanesulfonic acid, and 98.8 grams of o-cresol and 45.8 grams of o-sec-butylphenol. The mixture is stirred and heated to 100-105° C. for 20 hours. The reaction mixture is then drowned into 800 grams of ice and water mixture. The pH of the reaction mixture is then adjusted to 9-10 by addition of 25% sodium hydroxide while maintaining a temperature below 60° C. Aromatic® 200, 300 grams, is now added to the aqueous suspension of the mixture of phthaleins. The reaction mixture is made highly alkaline by addition of 225 grams of 25% sodium hydroxide and then esterified by slow addition of 321 grams n-hexanoic anhydride maintaining a temperature below 50° C. and a pH of 10 or higher. The reaction mixture is then stirred till esterification is complete, as determined by thin layer chromatography. The reaction mixture is then heated to 90° C. and transferred to a separatory funnel where the layers are allowed to separate. The lower aqueous phase is removed and discarded while the upper organic phase containing the mixture of esterified phthaleins is dried free of water by heating it under vacuum to a temperature of 120° C. The dried product is further diluted with Aromatic® 200 to a weight of 1000 grams. The product is then filtered to remove any suspended insoluble material.

Example 5

Preparation of Mixture of o-Cresolphthalein dihexanoate, o-Butylphthalein dihexanoate, o-Cresolphthalein diheptanoate, and o-Butylphthalein diheptanoate 100 grams of phthalic anhydride, 110 grams of methanesulfonic acid, and 98.8 grams of o-cresol and 45.8 grams of o-sec-butylphenol were stirred and heated to 100-105° C. for 20 hours. The reaction mixture is then drowned and the pH of the reaction mixture is adjusted to 9-10 by addition of 25% sodium hydroxide while maintaining a temperature below 60° C. Aromatic® 200, 300 grams, is now added to the aqueous suspension of the mixture of phthaleins. The reaction mixture is made highly alkaline by addition of 225 grams of 25% sodium hydroxide and then esterified by slow addition of a mixture of 171 grams n-heptanoic anhydride and 160.5 grams of hexanoic anhydride while maintaining a temperature below 50° C. and a pH of 10 or higher. When esterification is complete, the reaction mixture is then heated to 90° C. and transferred to a separatory funnel where the layers are allowed to separate. The lower aqueous phase is removed and discarded while the upper organic phase containing the mixture of esterified phthaleins is dried free of water by heating it under vacuum to a temperature of 120° C. The dried product is further diluted with Aromatic® 200 to a weight of 1000 grams. The product is then filtered to remove any suspended insoluble material.

Example 6

Preparation of Mixture of o-Cresolphthalein diheptanoate o-isopropylphthalein diheptanoate 100 grams of phthalic anhydride, 110 grams of methanesulfonic acid, and 98.8 grams of o-cresol and 41.5 grams of o-iso-propylphenol were stirred and heated to 100-105° C. for 20 hours. The reaction mixture is then drowned and the pH of the reaction mixture is adjusted to 9-10 by addition of 25% sodium hydroxide while maintaining a temperature below 60° C. Aromatic® 200, 300 grams, is now added to the aqueous suspension of the mixture of phthaleins. The reaction mixture is made highly alkaline by addition of 225 grams of 25% sodium hydroxide and then esterified by slow addition of 342 grams n-heptanoic anhydride while maintaining a temperature below 50° C. and a pH of 10 or higher. When esterification is complete, the reaction mixture is then heated to 90° C. and transferred to a separatory funnel where the layers are allowed to separate. The lower aqueous phase is removed and discarded while the upper organic phase containing the mixture of esterified phthaleins is dried free of water by heating it under vacuum to a temperature of 120° C. The dried product is further diluted with Aromatic® 200 to a weight of 1000 grams. The product is then filtered to remove any suspended insoluble material.

Example 7

Preparation of Mixed alkylphenolphthalein diester #7 (see Table 1)

The same procedure was followed as in Example 1 except 98.8 g of o-cresol and 41.5 g of o-isopropylphenol were used, and, 118.5 grams of butyric anhydride and 160.5 grams hexanoic anhydride were used instead of the 342 grams of heptanoic anhydride.

Example 8

Preparation of Mixed alkylphenolphthalein diester #8 (see Table 1)

The same procedure was followed as in Example 1 except 44.3 g of o-cresol, 61.5 g of o-sec-butylphenol, and 55.8 g of o-isopropylphenol were used, and, 237 g of butyric anhydride were used.

Example 9

Preparation of Mixed alkylphenolphthalein diester #9 (see Table 1)

The same procedure was followed as in Example 1 except 44.3 g of o'-cresol, 61.5 g of o-sec-butylphenol, and 55.8 g of o-isopropylphenol were used. Anhydride charge remained 342 g of heptanoic anhydride.

Example 10

Preparation of Mixed alkylphenolphthalein diester 10 (see Table 1)

The same procedure was followed as in Example 1 except 44.3 g of o-cresol, 61.5 g of o-sec-butylphenol, and 55.8 g of o-isopropylphenol were used, and, a mixture of 52.1 g butyric anhydride, 107 g hexanoic anhydride, and 114 g of heptanoic anhydride were used for the esterification.

The marker compositions comprising a marker mixture prepared in accordance with the above Examples were tested to evaluate their solubility effects (dispersion characteristic) and stability at low temperatures.

Test Procedures:
Preparation of the Marker Composition

The marker compositions are prepared by combining a marker mixture prepared in accordance with the above Examples with aromatic solvent and co-solvent (if any).

Storage Solubility Test

Storage solubility was tested on the marker composition by placing 100 g in a sealed container into a freezer. The temperature was fixed at 0° C. and examined periodically (i.e., daily) for precipitation.

Miscibility Test

The marker compositions were added drop-wise to 100 g of solvent (kerosene or diesel fuel). The systems were then observed if the marker compositions went into solution, or if they remained as a separate phase and clung to the sides of the beaker. Gentle agitation is employed although it makes no difference. A drop added will either fall to the bottom of the beaker (determined as showing poor miscibility) or will readily dissolve (showing miscibility).

Stability Test

The stability test was proceeded in kerosene (which is considered the worst case for solubility). 10% by weight marker composition is added to kerosene. This test is to provide a quantitative number to the miscibility result above. If no phase separation or precipitation is observed, the sample is determined as "stable."

Example 11-21

The marker compositions (as indicated by Examples 11-21) were prepared by combining the mixtures prepared from above Examples 1-10 with solvent in the formation as described in the table 2 below.

Comparative Example 1-3

For comparison, the prior art marker compositions (as indicated by Comparative Examples 1-3) were prepared by combining cresolphthalein dibutyrate, as taught in U.S. Pat. No. 6,482,651 (UCM, product name, " ") with solvent and co-solvent (N-octylpyrolidinone) in the formation as described in the table 2 below.

TABLE 2

Formulation of marker compositions

| | Active marker compound | Amount of Co-solvent in composition | Amount of active marker in composition | Amount of organic solvent in composition |
|---|---|---|---|---|
| Example 11 | Mixture prepared from Example 1 | ZERO | 20% | Quantity to 100% in total |
| Example 12 | Mixture prepared from Example 1 | ZERO | 25% | Quantity to 100% in total |
| Example 13 | Mixture prepared from Example 2 | ZERO | 20% | Quantity to 100% in total |
| Example 14 | Mixture prepared from Example 3 | ZERO | 20% | Quantity to 100% in total |
| Example 15 | Mixture prepared from Example 4 | ZERO | 20% | Quantity to 100% in total |
| Example 16 | Mixture prepared from Example 5 | ZERO | 20% | Quantity to 100% in total |
| Example 17 | Mixture prepared from Example 6 | ZERO | 20% | Quantity to 100% in total |
| Example 18 | Mixture prepared from Example 7 | ZERO | 20% | Quantity to 100% in total |
| Example 19 | Mixture prepared from Example 8 | ZERO | 20% | Quantity to 100% in total |
| Example 20 | Mixture prepared from Example 9 | ZERO | 20% | Quantity to 100% in total |

TABLE 2-continued

Formulation of marker compositions

| | Active marker compound | Amount of Co-solvent in composition | Amount of active marker in composition | Amount of organic solvent in composition |
|---|---|---|---|---|
| Example 21 | Mixture prepared from Example 10 | ZERO | 20% | Quantity to 100% in total |
| Comparative Example 1 | Cresolphthalein dibutyrate | 28% (or more) | 20% (or less) | Quantity to 100% in total |
| Comparative Example 2 | Cresolphthalein dibutyrate | <27% | 20% | Quantity to 100% in total |
| Comparative Example 3 | Cresolphthalein dibutyrate | 28% | >22% | Quantity to 100% in total |

The marker compositions comprising a marker mixture prepared in accordance with the above examples were tested to evaluate the storage stability, the miscibility and the stability according to the test procedures as described above. The test results are provided in the following table.

TABLE 3

Solubility Comparison:
Pure Phthalein Esters vs. Mixed Phthaleins and/or Mixed Esters

| | Storage stability at 0° C. | Miscibility with Kerosene or Diesel Fuel | Stability of a 10% solution in Kerosene |
|---|---|---|---|
| Example 11 | >3 months | Completely miscible | Completely stable |
| Example 12 | >3 months | Completely miscible | Completely stable |
| Example 13 | >3 months | Completely miscible | Completely stable |
| Example 14 | >3 months | Completely miscible | Completely stable |
| Example 15 | >3 months | Completely miscible | Completely stable |
| Example 16 | >3 months | Completely miscible | Completely stable |
| Example 17 | >3 months | Completely miscible | Completely stable |
| Example 18 | >3 months | Completely miscible | Completely stable |
| Example 19 | >3 months | Completely miscible | Completely stable |
| Example 20 | >3 months | Completely miscible | Completely stable |
| Example 21 | >3 months | Completely miscible | Completely stable |
| Comparative Example 1 | More than 3 months | Miscible | Not soluble |
| Comparative Example 2 | <7 days | Only miscible at very low concentration | Not soluble |
| Comparative Example 3 | <7 days | Only miscible at very low concentrations | Not soluble |

As shown in Table 3, the marker compositions comprising a mixture according to the present invention provide a marked improvement over prior art marker compounds (e.g., Comparative Examples 1-3) in that they may be manufactured without the use of any co-solvent. In addition, the test results of stability of a 10% solution shows that the mixture according to the present invention can be formulated at higher concentrations than is the case with prior art chemicals based of this improved solubility.

The invention having been thus described, it will be obvious that the same may be modified in many ways without departing from the spirit and scope of the invention as defined in the following claims.

The invention claimed is:

1. A marker composition comprising at least two different alkylated phenolphthalein ester compounds of formula I:

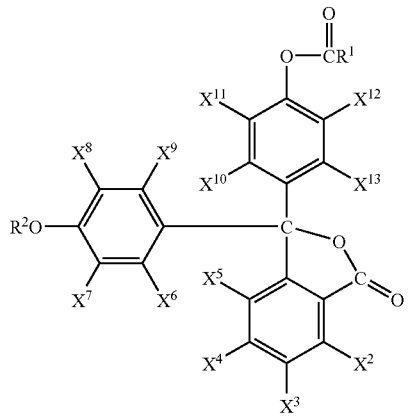

wherein $R^1$ represents a straight chain alkyl group having 1 to 11 carbon atoms;

$R^2$ represents a hydrogen atom or a group of the formula $C(O)R^4$ where $R^4$ is a hydrogen atom or a straight chain alkyl group having 1 to 11 carbon atoms;

X2-X5 independently represent hydrogen; X6-X13 is same or different, and represents hydrogen or a straight or branched chain alkyl group having 1 to 12 carbon atoms, wherein formulation of the composition does not require the use of any co-solvent.

2. The composition according to claim 1, wherein $R^1$ represents a straight chain alkyl group having 3 to 7 carbon atoms; and $R^2$ represents a hydrogen atom or a group of the formula $C(O)R^4$ where $R^4$ is a hydrogen atom or a straight chain alkyl group having 3 to 7 carbon atoms.

3. The composition according to claim 2, wherein $R^1$ represents a straight chain alkyl group having 3 to 6 carbon atoms; and $R^2$ represents a hydrogen atom or a group of the formula $C(O)R^4$ where $R^4$ is a hydrogen atom or a straight chain alkyl group having 3 to 6 carbon atoms.

4. The composition according to claim 3, wherein $R^1$ represents a straight chain alkyl group having 6 carbon atoms; and $R^2$ represents a hydrogen atom or a group of the formula $C(O)R^4$ where $R^4$ is a hydrogen atom or a straight chain alkyl group having 6 carbon atoms.

5. The composition according to claim 1, wherein $X^6$-$X^{13}$ is same or different, and represents hydrogen or a straight or branched chain alkyl group having 1 to 5 carbon atoms.

6. The composition according to claim 5, wherein one or two of $X^6$ to $X^9$ are alkyl group having 1 to 5 carbon atoms, one or two of $X^{10}$ to $X^{13}$ are alkyl group having 1 to 5 carbon atoms, and the other X groups are hydrogen.

7. The composition according to claim 5, wherein one of $X^7$ and $X^8$ is methyl, propyl or butyl, one of $X^{11}$ and $X^{12}$ is methyl, propyl or butyl, and other X groups are hydrogen.

8. The composition according to claim 1, wherein the mixture comprises at least three of alkylated phenolphthalein ester compounds.

9. The composition according to claim 1, wherein one of the alkylated phenolphthalein ester compounds in the mixture comprises at least about 10% by weight based on the total weight of the mixture, and another ester compound in the mixture comprises at least about 10% by weight based on the total weight of the mixture.

10. The composition according to claim 9, wherein one of the alkylated phenolphthalein ester compounds in the mixture comprises at least about 25% by weight based on the total weight of the mixture, and another ester compound in the mixture comprises at least about 25% by weight based on the total weight of the mixture.

11. The composition according to claim 1, comprising an aromatic solvent.

12. A marker composition, comprising:
about 42-99% by weight of an aromatic solvent;
about 1-30% by weight of a mixture comprising at least two different alkylated phenolphthalein ester compounds; and
about 0% by weight of co-solvent,
wherein the alkylated phenolphthalein ester compound is selected from the group of compounds represented by formula I:

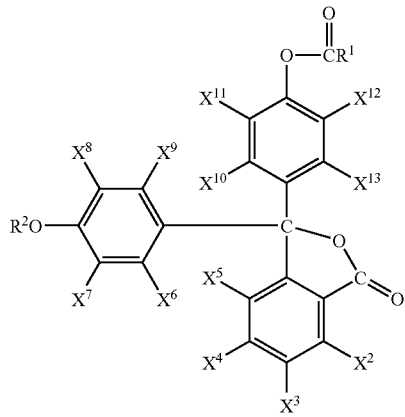

wherein $R^1$ represents a straight chain alkyl group having 1 to 11 carbon atoms;

$R^2$ represents a hydrogen atom or a group of the formula $C(O)R^4$ where $R^4$ is a hydrogen atom or a straight chain alkyl group having 1 to 11 carbon atoms;

X2-X5 independently represent hydrogen;

X6-X13 is same or different, and represents hydrogen or a straight or branched chain alkyl group having 1 to 12 carbon atoms.

* * * * *